(12) United States Patent
Qiu et al.

(10) Patent No.: US 11,491,472 B2
(45) Date of Patent: Nov. 8, 2022

(54) PREPARATION AND APPLICATION OF 4-METHYL-5-VINYLTHIAZOLYL POLYMERIC IONIC LIQUID

(71) Applicant: FU ZHOU UNIVERSITY, Fujian (CN)

(72) Inventors: Ting Qiu, Fujian (CN); Dongren Cai, Fujian (CN); Changshen Ye, Fujian (CN); Ling Li, Fujian (CN); Xiaoda Wang, Fujian (CN); Jinbei Yang, Fujian (CN); Zhixian Huang, Fujian (CN); Chen Yang, Fujian (CN); Hongxing Wang, Fujian (CN)

(73) Assignee: FU ZHOU UNIVERSITY, Fujian (CN)

( * ) Notice: Subject to any disclaimer, the term of this patent is extended or adjusted under 35 U.S.C. 154(b) by 0 days.

(21) Appl. No.: 16/607,101

(22) PCT Filed: Jun. 22, 2017

(86) PCT No.: PCT/CN2017/089555
§ 371 (c)(1),
(2) Date: Oct. 22, 2019

(87) PCT Pub. No.: WO2018/227650
PCT Pub. Date: Dec. 20, 2018

(65) Prior Publication Data
US 2020/0376473 A1    Dec. 3, 2020

(30) Foreign Application Priority Data
Jun. 15, 2017 (CN) .......................... 201710452401.4

(51) Int. Cl.
*B01J 31/10* (2006.01)
*B01J 31/02* (2006.01)
(Continued)

(52) U.S. Cl.
CPC .......... *B01J 31/10* (2013.01); *B01J 31/0244* (2013.01); *B01J 35/08* (2013.01); *C07C 67/03* (2013.01);
(Continued)

(58) Field of Classification Search
CPC ........ B01J 31/10; B01J 31/0244; B01J 35/08; C08F 228/06; C08F 28/06
See application file for complete search history.

(56) References Cited

U.S. PATENT DOCUMENTS 2,515,318 A * 7/1950 Schoene ................. C08F 28/06
526/257

FOREIGN PATENT DOCUMENTS

CN    102633929 A    8/2012
CN    103706396 A    4/2014
(Continued)

OTHER PUBLICATIONS

Bukowska, A., et al., Synthesis and characterization of new functionalized polymer-Fe3O4 nanocomposite particles, Express polymer letters, vol. 11, No. 1, pp. 2-13 (Year: 2017).*
(Continued)

*Primary Examiner* — Yate' K Cutliff

(57) ABSTRACT

Disclosed are a preparation method and application of a 4-methyl-5-vinylthiazolyl polymerized spherical ionic liquid catalyst. The method comprises: preparing a functional ionic liquid monomer successfully by taking 4-methyl-5-vinylthiazole as the matrix, and preparing the polymerized spherical ionic liquid from the monomer. The catalyst combines the advantages of both ionic liquid and the polymer, and has the characteristics of large specific surface area, high catalytic activity, high mass transfer rate, good selectivity, high stability, easy recycling and separating, environmental friendliness, wide industrial application prospect, etc. The
(Continued)

spherical ionic liquid is made into a novel catalytic packing and then put into a reactive distillation column for continuous reactive distillation of esterification and transesterification to realize the organic combination of the ionic liquid and the reactive distillation technology, achieving good catalytic activity, high product yield, environmental friendliness, and low corrosivity, which has great significance in realizing an environment-friendly process.

8 Claims, 3 Drawing Sheets

(51) Int. Cl.
   *B01J 35/08*     (2006.01)
   *C07C 67/03*     (2006.01)
   *C07C 67/08*     (2006.01)
   *C08F 228/06*    (2006.01)
   *C08F 28/06*     (2006.01)

(52) U.S. Cl.
   CPC .............. *C07C 67/08* (2013.01); *C08F 28/06* (2013.01); *C08F 228/06* (2013.01); *B01J 2231/49* (2013.01)

(56) References Cited

FOREIGN PATENT DOCUMENTS

| | | | |
|---|---|---|---|
| CN | 104492485 A | 4/2015 | |
| CN | 104492494 A | 4/2015 | |
| CN | 104492495 A | 4/2015 | |
| CN | 105131181 A | 12/2015 | |
| CN | 105461654 A * | 6/2016 | ............. B01J 31/10 |
| WO | 2014032004 A1 | 2/2014 | |

OTHER PUBLICATIONS

CN 105461654, Univ. Nanjing Forestry: Jiangsu Yida Chemical Co Ltd.; Benzothiazole ionic liquid and preparation method as well as application thereof; English Translation, 8 pages (Year: 2016).*

* cited by examiner

PREPARATION AND APPLICATION OF 4-METHYL-5-VINYLTHIAZOLYL POLYMERIC IONIC LIQUID

FIELD AND BACKGROUND OF THE INVENTION

1. Technical Field

The present invention belongs to the preparation and catalytic applications of ionic liquids, and particularly relates to the preparation and application of a 4-methyl-5-vinylthiazolyl polymerized ionic liquid catalyst.

2. Background

Esterification and transesterification are important organic synthesis reactions, which are widely used in the production of perfumes, dyes, solvents and pharmaceutical products. However, esterification and transesterification are reversible chemical reactions, which are subject to chemical equilibrium, generally resulting in a low conversion, causing a high subsequent separation load and producing a large amount of pollutant. As a result, in order to improve the conversion and reduce the energy consumption and pollutant emissions from the source, an environment-friendly chemical technology should be used to transform or replace traditional production processes. Reactive distillation is a chemical process in which a chemical reaction and a distillation separation are organically combined and simultaneously completed in one apparatus. It has two advantages. On one hand, since the chemical reaction and product separation are carried out simultaneously, the product formed by the reaction is promptly separated so that the reaction is always carried out in a non-equilibrium state, which can greatly improve the reaction conversion; on the other hand, the separation process of the reaction mixture and the catalyst can be omitted, reducing production cost greatly. Therefore, the reactive distillation process can greatly improve the production efficiency of these esterification and transesterification reactions, achieving the goal of an environment-friendly process.

Catalysts commonly used for esterification and transesterification are inorganic strong acids such as concentrated sulfuric acid, and inorganic strong bases such as sodium hydroxide. Although these conventional catalysts have high catalytic activity, they have problems such as high corrosivity, serious pollution, and difficulty in being separated from the reaction system. In recent years, with extensive research on the catalysts of esterification and transesterification, the heterogeneous solid acid-base catalysts have emerged. Although these solid materials solve the problems of separation and recovery of catalysts, they generally have the problems of complicated preparation process, low activity, and poor stability. Ionic liquid is a liquid substance composed entirely of ions at room temperature. It has the advantages of being almost non-volatile, wide liquid temperature range and adjustable structure. As a catalyst for esterification and transesterification, the conventional ionic liquid can effectively avoid the environmental pollution, equipment corrosion, but it is still difficult to be separated from the reaction system after reaction and has great loss. The polymerized ionic liquid, a multi-layer macroporous solid catalyst material, is synthesized via the free radical polymerization of the ionic liquid monomer, and possesses excellent properties of ionic liquid and polymer, like high catalytic activity, good reusability, low catalyst dosage and separating the catalyst and product only by a simple physical separation method. At present, the studies on polymerized ionic liquids are mostly concentrated on vinylimidazolyl ionic liquids, and there are few reports about vinylthiazolyl ionic liquids. The structure of thiazolyl is very similar with that of imidazolyl, just substituting the non-double bond N atom of imidazolyl with a S atom. Compared to the N atom, the S atom has electronegativity closer to the electronegativity of the C atom, which makes the heterocyclic ring more stable. Therefore, the 4-methyl-5-vinylthiazolyl polymerized ionic liquid is superior to the imidazolyl based polymerized ionic liquid in catalytic activity and stability.

SUMMARY OF THE INVENTION

In view of the disadvantages in the prior art, the objective of the present invention is to provide a 4-methyl-5-vinylthiazolyl polymerized spherical ionic liquid catalyst with high catalytic activity, good hydrothermal stability, simple preparation process, easy recovery for esterification and transesterification, and good reusability. And the prepared 4-methyl-5-vinylthiazolyl polymerized spherical ionic liquid is made into a novel catalytic packing and then put into a reactive distillation column for the continuous reactive distillation processes of esterification and transesterification.

To realize the above goal, the present invention adopts the following technical solutions:

The structural formula of the 4-methyl-5-vinylthiazolyl polymerized spherical ionic liquid catalyst is as follow:

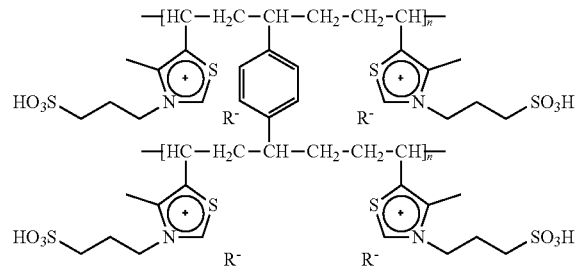

wherein R— refers to one of hydrogen sulfate ion and trifluoromethane sulfonate ion, and n refers to degree of polymerization (n=2500-3000).

The preparation method of the 4-methyl-5-vinylthiazolyl polymerized spherical ionic liquid catalyst includes the following steps:

(1) Synthesis of a zwitterion. Ethyl acetate as the solvent, the reaction of 1,3-propanesultone and 4-methyl-5-vinylthiazole is conducted to obtain the zwitterion.

(2) Synthesis of the ionic liquid monomer. The ionic liquid monomer is prepared via the reaction of the zwitterion obtained in step (1) and Brønsted acid.

(3) Synthesis of the polymerized spherical ionic liquid. Firstly, the ionic liquid monomer prepared in step (2), divinylbenzene and $Fe_3O_4$@MPS are ultrasonically dispersed in the solvent. Then, the initiator is added into the mixture. Finally, the reaction system is heated for polymerization to obtain the polymerized spherical ionic liquid.

More specifically, the preparation method of the 4-methyl-5-vinylthiazolyl polymerized spherical ionic liquid catalyst includes the following steps:

(1) Synthesis of a zwitterion. Firstly, in an ice water bath, 0.05-0.1 mol of 1,3-propanesultone is dissolved in 50-300 mL of ethyl acetate. Next, stirring thoroughly, 0.05-0.1 mol of 4-methyl-5-vinylthiazole is added dropwise into the above mixture. Then, the reaction is conducted to generate a zwitterion (solid product) at 40-90° C. for 12-48 hours. Finally, after suction filtration, the solid product is washed by ethyl acetate for three times and dried in the vacuum drying oven for 6-12 hours.

(2) Synthesis of an ionic liquid monomer. Firstly, in an ice water bath, the zwiterion obtained in step (1) is dissolved in 100-400 mL of deionized water. Next, stirring thoroughly, the equimolar Brønsted acid is added dropwise into the above mixture. Then, the reaction is conducted in the presence of nitrogen gas at 50-90° C. for 8-36 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 8-12 hours.

(3) Synthesis of a polymerized spherical ionic liquid. Firstly, 0.01-0.05 mol of the ionic liquid monomer prepared in step (2), 0.002-0.04 mol of divinylbenzene and 1-12 g of $Fe_3O_4$@MPS template nanoparticles are dispersed in 40-200 mL of dimethyl sulfoxide (DMSO), and ultrasonication is carried out for the mixture for 15-30 min. Then, the nitrogen is introduced into the reaction system to remove the oxygen. Stirring thoroughly, 0.05-0.8 g of azobisisobutyronitrile is added into the mixture. The reaction system is heated to 50-80° C. to conduct the polymerization for 8-24 hours in the presence of nitrogen, and after suction filtration, the solid product is washed by DMSO for 3-5 times. Finally, the solid product is dispersed in DMSO, and 10-50 mL of concentrated hydrochloric acid is added dropwise into the DMSO dispersion. Via ultrasonication for 20-40 min, being removed the solvent by suction filtration, being washed by DMSO for several times, and being dried in the vacuum drying oven, the polymerized spherical ionic liquid is obtained.

Preferably, the preparation method of the 4-methyl-5-vinylthiazolyl polymerized spherical ionic liquid catalyst includes the following steps:

(1) Synthesis of a zwitterion. Firstly, in an ice water bath, 0.05-0.1 mol of 1,3-propanesultone is dissolved in 100-250 mL of ethyl acetate. Next, stirring thoroughly, 0.05-0.1 mol of 4-methyl-5-vinylthiazole is added dropwise into the above mixture. Then, the reaction is conducted to generate a zwitterion (solid product) at 60-80° C. for 24-48 hours. Finally, after suction filtration, the solid product is washed by ethyl acetate for three times and dried in the vacuum drying oven for 8-12 hours.

(2) Synthesis of an ionic liquid monomer. Firstly, in an ice water bath, the zwitterion obtained in step (1) is dissolved in 200-350 mL of deionized water. Next, stirring thoroughly, equimolar Brønsted acid is added dropwise into the above mixture. Then, the reaction is conducted in the presence of nitrogen gas at 70-90° C. for 12-24 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 8-12 hours.

(3) Synthesis of a polymerized spherical ionic liquid. Firstly, 0.01-0.05 mol of the ionic liquid monomer prepared in step (2), 0.004-0.02 mol of divinylbenzene and 4-10 g of $Fe_3O_4$@MPS template nanoparticles are dispersed in 40-200 mL of dimethyl sulfoxide (DMSO), and ultrasonication is carried out for the mixture for 15-30 min. Then, the nitrogen is introduced into the reaction system to remove the oxygen. Stirring thoroughly, 0.1-0.6 g of azobisisobutyronitrile is added into the mixture. The reaction system is heated to 60-80'C to conduct the polymerization for 18-24 hours in the presence of nitrogen, and after suction filtration, the solid product is washed by DMSO for 3-5 times. Finally, the solid product is dispersed in DMSO, and 10-50 mL of concentrated hydrochloric acid is added dropwise into the DMSO dispersion. Via ultrasonication for 20-40 min, being removed the solvent by suction filtration, being washed by DMSO for several times, and being dried in the vacuum drying oven, the polymerized spherical ionic liquid is obtained.

The applications of the 4-methyl-5-vinylthiazolyl polymerized spherical ionic liquid catalyst in continuous reactive distillation processes of esterification and transesterification: the 4-methyl-5-vinylthiazolyl polymerized spherical ionic liquid is made into a structured catalytic packing and then put into a reactive distillation column for the continuous reactive distillation processes of esterification and transesterification.

Specific steps are as follow:

(1) The 4-methyl-5-vinylthiazolyl polymerized spherical ionic liquid catalyst is put into catalyst cloth bags, and the solid catalyst filled in each cloth bag accounts for 70% to 90% of the bag volume. Each cloth bag has a length of 60 mm to 80 mm and a width of 4 mm to 6 mm.

(2) The catalyst cloth bags are combined with a structured corrugated packing to form structured catalytic packing units. The catalyst cloth bags and the structured corrugated packing are alternately arranged in each catalytic packing unit, and the horizontal inclination angle of each catalyst cloth bag is 45°-60'. In the case where multiple layers of catalytic packing units are placed in a reactive distillation column, the catalyst cloth bags and the structured corrugated packing are arranged in a staggered manner between the upper and lower catalytic units with opposite inclination angles, thus generally forming a structure in which the catalyst cloth bags and the structured corrugated packing are alternately and cross-like arranged in both the lateral and longitudinal directions, as shown in FIG. 1.

(3) The continuous reactive distillation process is applied to the esterification system of propionic acid and n-propanol and the transesterification system of isopropyl acetate and methanol.

With the adoption of the above technical solutions, the beneficial effects are as follow:

1. According to the present invention, the polymerized spherical ionic liquid is synthesized via the free radical polymerization of the ionic liquid monomer. The polymerized spherical ionic liquid is a multi-layer macroporous solid catalyst material, and possesses the excellent properties of ionic liquid and polymer, like high catalytic activity, good reusability, low catalyst dosage and separating the catalyst and product only by a simple physical separation method. Moreover, compared with the imidazolyl based polymerized ionic liquid, the polymerized spherical ionic liquid is greatly improved in stability.

2. According to the present invention, the 4-methyl-5-vinylthiazolyl polymerized spherical ionic liquid is made into a novel catalytic packing and then put into a reactive distillation column for the continuous reactive distillation processes of esterification and transesterification to realize the organic combination of the ionic liquid and the reactive distillation technology, achieving good catalytic activity, high product yield, environmental friendliness, no pollution and low corrosivity, which has the great significance in realizing an environment-friendly process, and thus being extremely competitive.

DESCRIPTION OF THE PREFERRED EMBODIMENTS

Figure 1:
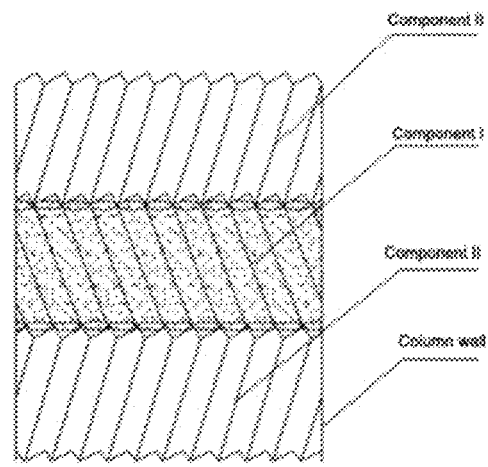
FIG. 1 shows a packing structure of the structured catalytic packing in the reactive distillation column.

The present invention will be described in further detail with reference to specific embodiments.

The structural formula of a 4-methyl-5-vinylthiazolyl polymerized spherical ionic liquid catalyst is as follow:

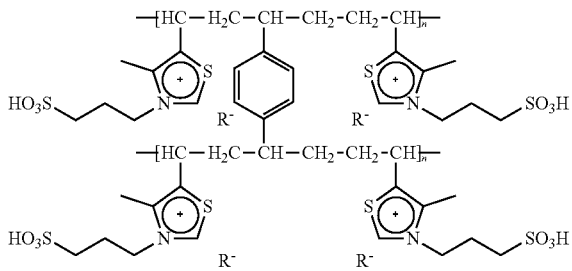

wherein R— refers to one of hydrogen sulfate ion and trifluoromethane sulfonate ion, and n refers to degree of polymerization.

The preparation method of the 4-methyl-1-vinylthiazolyl polymerized spherical ionic liquid catalyst includes the following steps:

(1) Synthesis of a zwitterion. Ethyl acetate as the solvent, the reaction of 1,3-propanesultone and 4-methyl-5-vinylthiazole is conducted to obtain the zwitterion.

(2) Synthesis of an ionic liquid monomer. The ionic liquid monomer is prepared via the reaction of the zwitterion obtained in step (1) and Brønsted acid.

(3) Synthesis of a polymerized spherical ionic liquid. Firstly, the ionic liquid monomer prepared in step (2), divinylbenzene and $Fe_3O_4$@MPS are ultrasonically dispersed in the solvent. Then, the initiator is added into the mixture. Finally, the reaction system is heated for polymerization to obtain a polymerized spherical ionic liquid.

More specifically, the preparation method of the 4-methyl-5-vinylthiazolyl polymerized spherical ionic liquid catalyst includes the following steps:

(1) Synthesis of a zwitterion. Firstly, in an ice water bath, 0.05-0.1 mol of 1,3-propanesultone is dissolved in 50-300 mL of ethyl acetate. Next, stirring thoroughly, 0.05-0.1 mol of 4-methyl-5-vinylthiazole is added dropwise into the above mixture. Then, the reaction is conducted to generate a zwitterion (solid product) at 40-90° C. for 12-48 hours. Finally, after suction filtration, the solid product is washed by ethyl acetate for three times and dried in the vacuum drying oven for 6-12 hours.

(2) Synthesis of an ionic liquid monomer. Firstly, in an ice water bath, the zwitterion obtained in step (1) is dissolved in 100-400 mL of deionized water. Next, stirring thoroughly, the equimolar Brønsted acid is added dropwise into the above mixture. Then, the reaction is conducted in the presence of nitrogen gas at 50-90° C. for 8-36 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 8-12 hours.

(3) Synthesis of a polymerized spherical ionic liquid. Firstly, 0.01-0.05 mol of the ionic liquid monomer prepared in step (2), 0.002-0.04 mol of divinylbenzene and 1-12 g of $Fe_3O_4$@MPS template nanoparticles are dispersed in 40-200 mL of dimethyl sulfoxide (DMSO), and ultrasonication is carried out for the mixture for 15-30 min. Then, the nitrogen is introduced into the reaction system to remove the oxygen. Stirring thoroughly, 0.05-0.8 g of azobisisobutyronitrile is added into the mixture. The reaction system is heated to 50-80° C. to conduct the polymerization for 8-24 hours in the presence of nitrogen, and after suction filtration, the solid product is washed by DMSO for 3-5 times. Finally, the solid product is dispersed in DMSO, and 10-50 mL of concentrated hydrochloric acid is added dropwise into the DMSO dispersion. Via ultrasonication for 20-40 min, being removed the solvent by suction filtration, being washed by DMSO for several times, and being dried in the vacuum drying oven, the polymerized spherical ionic liquid is obtained.

Preferably, the preparation method of the 4-methyl-5-vinylthiazolyl polymerized spherical ionic liquid catalyst includes the following steps:

(1) Synthesis of a zwitterion. Firstly, in an ice water bath, 0.05-0.1 mol of 1,3-propanesultone is dissolved in 100-250 mL of ethyl acetate. Next, stirring thoroughly, 0.05-0.1 mol of 4-methyl-5-vinylthiazole is added dropwise into the above mixture. Then, the reaction is conducted to generate a zwitterion (solid product) at 60-80° C. for 24-48 hours. Finally, after suction filtration, the solid product is washed by ethyl acetate for three times and dried in the vacuum drying oven for 8-12 hours.

(2) Synthesis of an ionic liquid monomer. Firstly, in an ice water bath, the zwitterion obtained in step (1) is dissolved in 200-350 mL of deionized water. Next, stirring thoroughly, equimolar Brønsted acid is added dropwise into the above mixture. Then, the reaction is conducted in the presence of nitrogen gas at 70-90° C. for 12-24 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 8-12 hours.

(3) Synthesis of a polymerized spherical ionic liquid. Firstly, 0.01-0.05 mol of the ionic liquid monomer prepared in step (2), 0.004-0.02 mol of divinylbenzene and 4-10 g of Fe$_3$O$_4$@MPS template nanoparticles are dispersed in 40-200 mL of dimethyl sulfoxide (DMSO), and ultrasonication is carried out for the mixture for 15-30 min. Then, the nitrogen is introduced into the reaction system to remove the oxygen. Stirring thoroughly, 0.1-0.6 g of azobisisobutyronitrile is added into the mixture. The reaction system is heated to 60-80° C. to conduct the polymerization for 18-24 hours in the presence of nitrogen, and after suction filtration, the solid product is washed by DMSO for 3-5 times. Finally, the solid product is dispersed in DMSO, and 10-50 mL of concentrated hydrochloric acid is added dropwise into the DMSO dispersion. Via ultrasonication for 20-40 min, being removed the solvent by suction filtration, being washed by DMSO for several times, and being dried in the vacuum drying oven, the polymerized spherical ionic liquid is obtained.

The applications of the 4-methyl-5-vinylthiazolyl polymerized spherical ionic liquid catalyst in continuous reactive distillation processes of esterification and transesterification: the 4-methyl-5-vinylthiazolyl polymerized spherical ionic liquid is made into a structured catalytic packing and then put into a reactive distillation column for the continuous reactive distillation processes of esterification and transesterification.

Specific steps are as follows:

(1) The 4-methyl-5-vinylthiazolyl polymerized spherical ionic liquid catalyst is put into catalyst cloth bags, and the solid catalyst filled in each cloth bag accounts for 70% to 90% of the bag volume. Each cloth bag has a length of 60 mm to 80 mm and a width of 4 mm to 6 mm.

(2) The catalyst cloth bags are combined with a structured corrugated packing to form structured catalytic packing units. The catalyst cloth bags and the structured corrugated packing are alternately arranged in each catalytic packing unit, and the horizontal inclination angle of each catalyst cloth bag is 45°-60°. In the case where multiple layers of catalytic packing units are placed in a reactive distillation column, the catalyst cloth bags and the structured corrugated packing are arranged in a staggered manner between the upper and lower catalytic units with opposite inclination angles, thus generally forming a structure in which the catalyst cloth bags and the structured corrugated packing are alternately and cross-like arranged in both the lateral and longitudinal directions.

(3) The continuous reactive distillation process is applied to the esterification system of propionic acid and n-propanol and the transesterification system of isopropyl acetate and methanol.

Embodiment 1

The structural formula of a 4-methyl-5-vinylthiazolyl polymerized spherical ionic liquid catalyst is as follow:

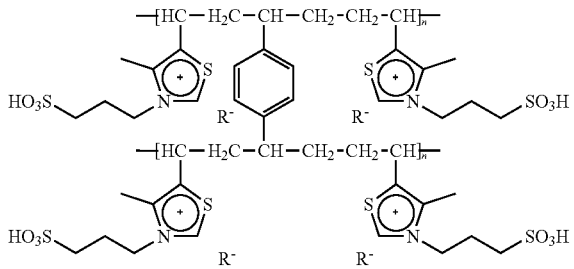

wherein R- refers to trifluoromethane sulfonate ion.

The preparation method of the 4-methyl-5-vinylthiazolyl polymerized spherical ionic liquid catalyst includes the following steps:

(1) Synthesis of a zwitterion. Firstly, in an ice water bath, 0.1 mol of 1,3-propanesultone is dissolved in 250 mL of ethyl acetate. Next, stirring thoroughly, 0.1 mol of 4-methyl-5-vinylthiazole is added dropwise into the above mixture. Then the reaction is conducted to generate a zwitterion (solid product) at 60° C. for 48 hours. Finally, after suction filtration, the solid product is washed by ethyl acetate for three times and dried in the vacuum drying oven for 12 hours.

Figure 2:
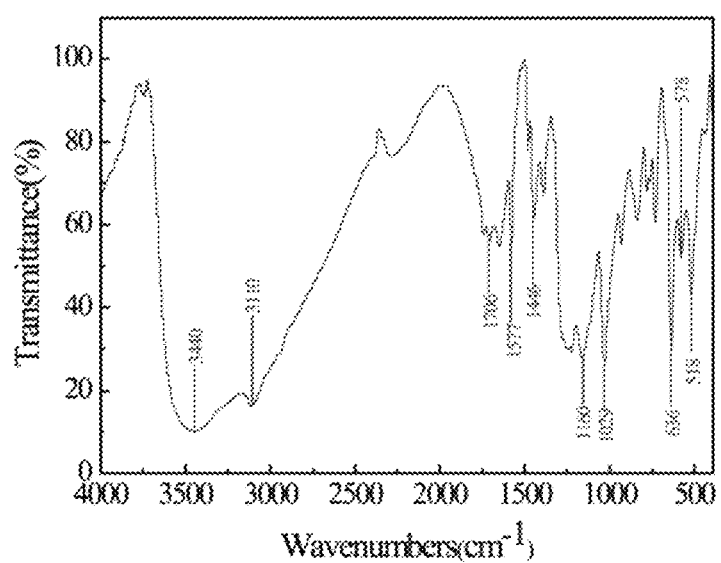
FIG. 2 is an infrared spectrum of an ionic monomer prepared in Embodiment 1.

(2) Synthesis of an ionic liquid monomer. Firstly, in an ice water bath, the zwitterion obtained in step (1) is dissolved in 350 mL of deionized water. Next, stirring thoroughly, the equimolar trifluoromethanesulfonic acid is added dropwise into the above mixture. Then, the reaction is conducted in the presence of nitrogen gas at 70° C. for 24 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 8 hours. The infrared characterization of the ionic liquid monomer is shown in FIG. 2.

Figure 4:
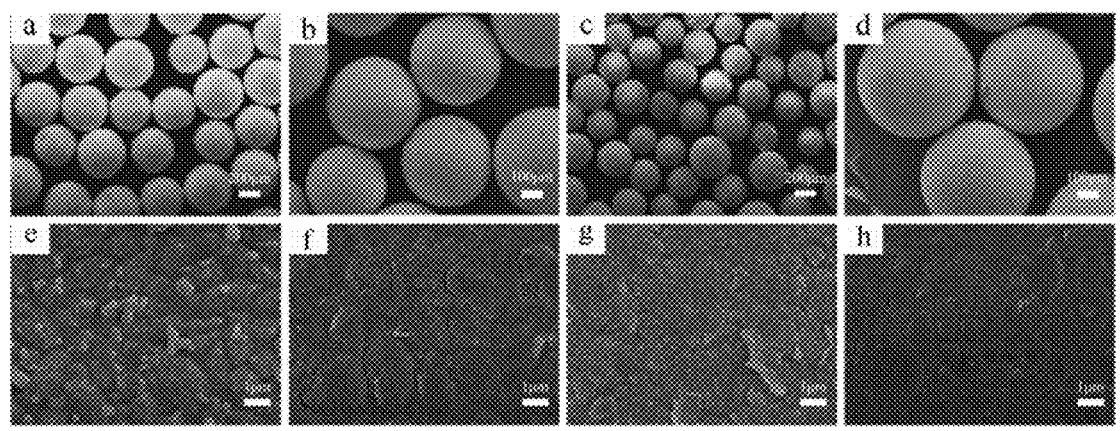
FIG. 4 shows SEM graphs of polymerized ionic liquids prepared in Embodiment 1 and Embodiment 2, where a, b, e and f is the SEM graphs of trifluoromethanesulfonic acid based polymerized ionic liquids; c, d, g and h is the SEM graphs of sulfuric acid based polymerized ionic liquids.
Figure 5:
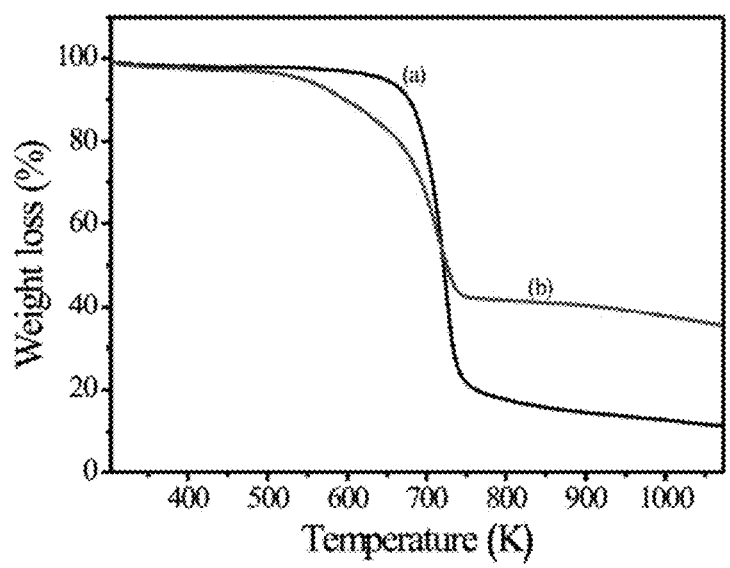
FIG. 5 is a thermogravimetric (TG) analysis chart of the polymerized ionic liquid prepared in Embodiment 1; (a) trifluoromethanesulfonic acid based polymerized ionic liquid; (b) sulfuric acid based polymerized ionic liquid.
Figure 6:
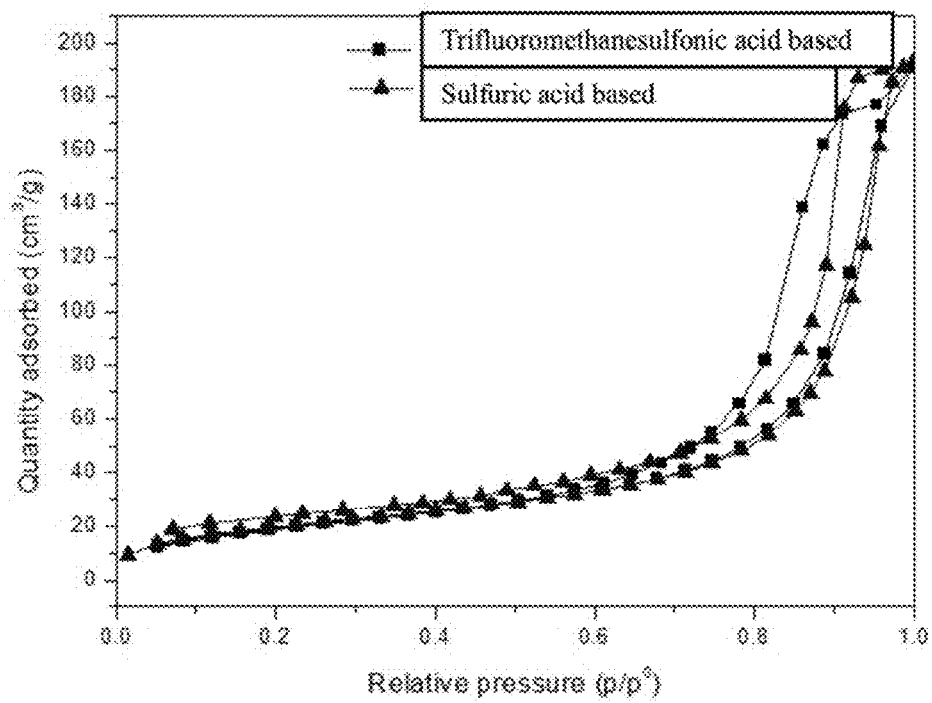
FIG. 6 is a specific surface area diagram (BET) chart of the polymerized ionic liquid prepared in Embodiment 1.

(3) Synthesis of a polymerized spherical ionic liquid. Firstly, 0.01 mol of the ionic liquid monomer prepared in step (2), 0.004 mol of divinylbenzene and 4 g of Fe$_3$O$_4$@MPS template nanoparticles are dispersed in 40 mL of dimethyl sulfoxide (DMSO), and ultrasonication is carried out for the mixture for 15 min. Then, the nitrogen is introduced into the reaction system to remove the oxygen. Stirring thoroughly, 0.1 g of azobisisobutyronitrile is added into the mixture. The reaction system is heated to 60° C. to conduct the polymerization for 18 hours in the presence of nitrogen, and after suction filtration, the solid product is washed by DMSO for 3 times. Finally, the solid product is dispersed in DMSO, and 10 mL of concentrated hydrochloric acid is added dropwise into the DMSO dispersion. Via ultrasonication for 20 min, being removed the solvent by suction filtration, being washed by DMSO for several times, and being dried in a vacuum drying oven, the polymerized spherical ionic liquid is obtained. The SEM graph, TG analysis chart and BET chart of the polymerized ionic liquid are shown in FIG. 4, FIG. 5 and FIG. 6, respectively.

Application Embodiment 1

The application of the 4-methyl-5-vinylthiazolyl polymerized spherical ionic liquid catalyst prepared in Embodiment 1 in a continuous reactive distillation process of esterification of propionic acid and n-propanol includes the following steps:

(1) The 4-methyl-5-vinylthiazolyl polymerized spherical ionic liquid catalyst is put into catalyst cloth bags, and the solid catalyst filled in each cloth bag accounts for 70% of the bag volume. Each cloth bag has a length of 60 mm and a width of 4 mm.

(2) The catalyst cloth bags are combined with a structured corrugated packing to form structured catalytic packing units. The catalyst cloth bags and the structured corrugated packing are alternately arranged in each catalytic packing unit, and the horizontal inclination angle of each catalyst cloth bag is 45°. In the case where multiple layers of catalytic packing units are placed in a reactive distillation column, the catalyst cloth bags and the structured corrugated packing are arranged in a staggered manner between the upper and lower catalytic units with opposite inclination angles, thus generally forming a structure in which the catalyst cloth bags and the structured corrugated packing are alternately and cross-like arranged in both the lateral and longitudinal directions, as shown in FIG. 1.

(3) The specific process of continuous reactive distillation of propionic acid and n-propanol: after being preheated to 50° C., propionic acid and n-propanol are fed in the reactive distillation column from the top and bottom of the catalytic packing layer respectively, wherein the feed molar ratio of the propionic acid to the n-propanol is 1:2, the feed flow of the n-propanol is 1.5 mol/h, the reflux ratio is 1.5, the reaction temperature is 100° C. the reaction pressure is 1 bar, and the yield of propyl propanoate is 99.10% under the steady-state operation condition. After 100 hours of continuous operation, the yield of the n-propyl propionate is still maintained at about 98.90%, indicating that the 4-methyl-5-vinylthiazolyl polymerized spherical ionic liquid catalyst has good stability.

Embodiment 2

The structural formula of a 4-methyl-5-vinylthiazolyl polymerized spherical ionic liquid catalyst is as follow:

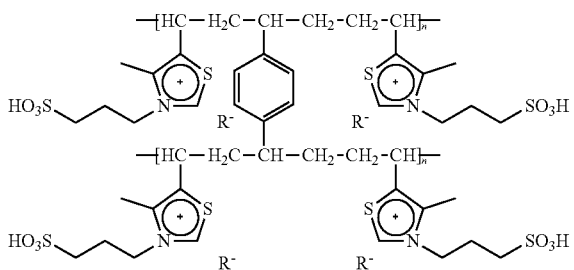

wherein R— refers to hydrogen sulfate ion.

The preparation method of the 4-methyl-5-vinythiazolyl polymerized spherical ionic liquid catalyst includes the following steps:

(1) Synthesis of a zwitterion. Firstly, in an ice water bath, 0.08 mol of 1,3-propanesultone is dissolved in 100 mL of ethyl acetate. Next, stirring thoroughly, 0.08 mol of 4-methyl-5-vinylthiazole is added dropwise into the above mixture. Then, the reaction is conducted to generate a zwitterion (solid product) at 80'C for 24 hours. Finally, after suction filtration, the solid product is washed by ethyl acetate for three times and dried in the vacuum drying oven for 8 hours.

Figure 3:
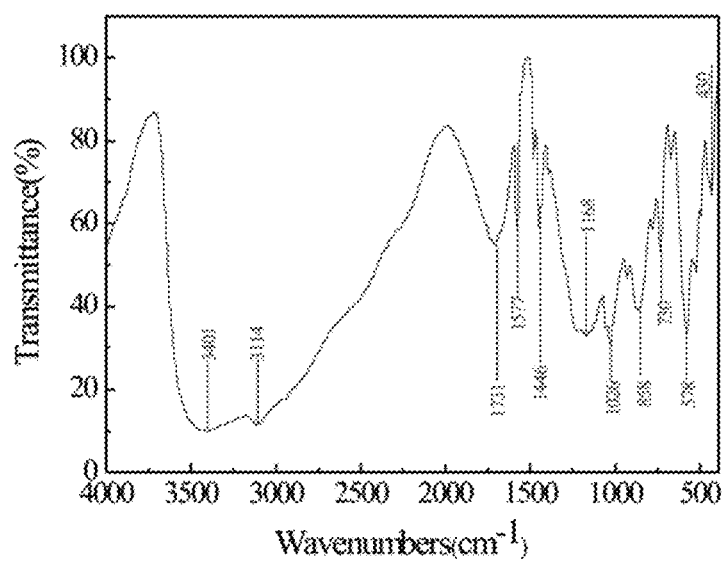
FIG. 3 is an infrared spectrum of an ionic monomer prepared in Embodiment 2.

(2) Synthesis of an ionic liquid monomer. Firstly, in an ice water bath, the zwitterion obtained in step (1) is dissolved in 200 mL of deionized water. Next, stirring thoroughly, the equimolar concentrated sulfuric acid is added dropwise into the above mixture. Then, the reaction is conducted in the presence of nitrogen gas at 90° C. for 12 hours. Finally, the water is removed from the reaction system by rotary evaporation, obtaining the viscous liquid (ionic liquid monomer). And the ionic liquid monomer is washed by ethyl acetate, the ethyl acetate is then removed by rotary evaporation, and the ionic liquid monomer is dried in the vacuum drying oven for 12 hours. The infrared characterization of the ionic liquid monomer is shown in FIG. 3.

(3) Synthesis of a polymerized spherical ionic liquid. Firstly, 0.05 mol of the ionic liquid monomer prepared in step (2), 0.02 mol of divinylbenzene and 10 g of $Fe_3O_4$@MPS template nanoparticles are dispersed in 200 mL of dimethyl sulfoxide (DMSO), and ultrasonication is carried out for the mixture for 30 min. Then, the nitrogen is introduced into the reaction system to remove the oxygen. Stirring thoroughly, 0.6 g of azobisisobutyronitrile is added into the mixture. The reaction system is heated to 80° C. to conduct the polymerization for 24 hours in the presence of nitrogen, and after suction filtration, the solid product is washed by DMSO for 5 times. Finally, the solid product is dispersed in DMSO, and 50 mL of concentrated hydrochloric acid is added dropwise into the DMSO dispersion. Via ultrasonication for 40 min, being removed the solvent by suction filtration, being washed by DMSO for several times, and being dried in a vacuum drying oven, the polymerized spherical ionic liquid is obtained.

Application Embodiment 2

The application of the 4-methyl-5-vinylthiazolyl polymerized spherical ionic liquid catalyst prepared in Embodiment 2 in a continuous reactive distillation process of transesterification between isopropyl acetate and methanol includes the following steps:

(1) The 4-methyl-5-vinylthiazolyl polymerized spherical ionic liquid catalyst is put into catalyst cloth bags, and the solid catalyst filled in each cloth bag accounts for 90% of the bag volume. Each cloth bag has a length of 80 mm and a width of 6 mm.

(2) The catalyst cloth bags are combined with a structured corrugated packing to form structured catalytic packing units. The catalyst cloth bags and the structured corrugated packing are alternately arranged in each catalytic packing unit, and the horizontal inclination angle of each catalyst cloth bag is 60°. In the case where multiple layers of catalytic packing units are placed in a reactive distillation column, the catalyst cloth bags and the structured corrugated packing are arranged in a staggered manner between the upper and lower catalytic units with opposite inclination angles, thus generally forming a structure in which the catalyst cloth bags and the structured corrugated packing are alternately and cross-like arranged in both the lateral and longitudinal directions, as shown in FIG. 1.

(3) The specific process of continuous reactive distillation of isopropyl acetate and methanol: after being preheated to 45° C., isopropyl acetate and methanol are respectively fed into the reactive distillation column from the top and bottom of the catalytic packing layer, wherein the feed molar ratio of the isopropyl acetate and the methanol is 1:3, the feed flow of the methanol is 2.4 mol/h, the reflux ratio is 1.8, the reaction temperature is 80° C., the reaction pressure is 3 bar, and the yield of isopropanol is 99.54% under the steady-state operation condition. After 100 hours of continuous operation, the yield of the isopropanol is still maintained at about 99.50%, indicating that the 4-methyl-5-vinylthiazolyl polymerized spherical ionic liquid catalyst has good stability.

Finally, it should be noted that the above-mentioned embodiments are merely specific embodiments of the present invention and used for explaining the technical solutions of the present invention rather than limiting them, and the scope of the present invention is not limited thereto. Although the present invention is described in detail with reference to the foregoing embodiments, those of ordinary skill in the art should understand that any one skilled in the art can still make modifications or readily conceive of changes to the technical solutions described in the foregoing embodiments, or make equivalent substitutions for some of the technical features within the technical scope disclosed by the present invention; and these modifications, changes or substitutions should not cause the essence of the corresponding technical solutions to depart from the spirit and scope of the technical solutions of the embodiments of the present invention. They all should fall within the scope of the present invention. Therefore, the scope of the present invention should be defined by the scope of the appended claims.

The invention claimed is:

1. A structural formula of 4-methyl-5-vinylthiazolyl polymerized spherical ionic liquid:

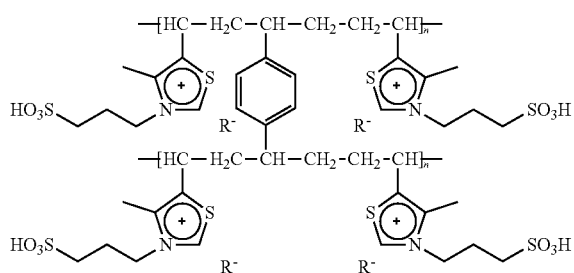

wherein R⁻ refers to one of hydrogen sulfate ion or trifluoromethane sulfonate ion, and n refers to degree of polymerization, n=2500-3000.

2. A preparation method of 4-methyl-5-vinylthiazolyl polymerized spherical ionic liquid catalyst according to claim 1, comprising the following steps:

Step (1) dissolving 0.05-0.1 mol of 1,3-propanesultone in 50-300 mL of ethyl acetate in an ice water bath, stirring thoroughly, adding 0.05-0.1 mol of 4-methyl-5-vinylthiazole dropwise into the above mixture, then, conducting the reaction to generate a zwitterion at 40-90° C. for 12-48 hours, finally, after suction filtration, washing the zwitterion by ethyl acetate for three times and drying in the vacuum drying oven for 6-12 hours;

Step (2) dissolving the zwitterion obtained in step (1) in 100-400 mL of deionized water in an ice water bath, stirring thoroughly, adding an equimolar Brønsted acid dropwise into the above mixture, then, conducting the reaction in the presence of nitrogen gas at 50-90° C. for 8-36 hours, finally, removing the water from the reaction system by rotary evaporation to obtain an ionic liquid monomer, and washing the ionic liquid monomer by ethyl acetate, removing the ethyl acetate by rotary evaporation, and drying the ionic liquid monomer in the vacuum drying oven for 8-12 hours;

Step (3) dispersing 0.01-0.05 mol of the ionic liquid monomer prepared in step (2), 0.002-0.04 mol of divinylbenzene and 1-12 g of Fe₃O₄@MPS template nanoparticles in 40-200 mL of dimethyl sulfoxide, reacting under ultrasonication for 15-30 min, then, introducing nitrogen into the reaction system to remove the oxygen, stirring thoroughly, adding 0.05-0.8 g of azobisisobutyronitrile into the mixture, heating the reaction system to 50-80° C. to conduct the polymerization for 8-24 hours in the presence of nitrogen, after suction filtration, then obtaining the solid product, washing by DMSO for 3-5 times, finally, dispersing the solid product in DMSO, adding 10-50 mL of concentrated hydrochloric acid dropwise into the DMSO dispersion, via ultrasonication for 20-40 min, removing the solvent by suction filtration, washing by DMSO for several times, drying in the vacuum drying oven, obtaining the polymerized spherical ionic liquid.

3. The preparation method of the 4-methyl-5-vinythiazolyl polymerized spherical ionic liquid catalyst according to claim 2, wherein the Brønsted acid in the step (2) is sulfuric acid or trifluoromethanesulfonic acid.

4. Application of the 4-methyl-5-vinylthiazolyl polymerized spherical ionic liquid catalyst according to claim 1 in distillation processes of esterification and transesterification, wherein making the 4-methyl-5-vinylthiazolyl polymerized spherical ionic liquid into a structured catalytic packing and then putting into a reactive distillation column for the continuous reactive distillation processes of esterification and transesterification.

5. The application according to claim 4, wherein the structured catalytic packing is composed of catalytic packing units, each catalytic packing unit is composed of a component I and a component II, and the component I and the component II are alternately arranged, inclined in opposite directions and tied up into a cylindrical shape to form a catalytic packing unit; the component I is a catalyst cloth bag filled with the 4-methyl-5-vinylthiazolyl polymerized spherical ionic liquid, and the component II is a structured corrugated packing.

6. The application according to claim 5, wherein the catalyst cloth bag is sewn by using silk cloth, nylon cloth or polyester cloth, and the cloth bag has a length of 60 mm to 80 mm and a width of 4 mm to 6 mm and the 4-methyl-5-vinylthiazolyl polymerized spherical ionic liquid filled in the cloth bag accounts for 70% to 90% of the bag volume.

7. The application according to claim 5, wherein the component I and the component II are alternately arranged in each catalytic packing unit, and the horizontal inclination angle of the component I is 45° to 60°; and in the case where multiple layers of catalytic packing units are placed in the reactive distillation column, the component I and the component II are arranged in a staggered manner between the upper and lower catalytic units with opposite inclination angles, thus generally forming a structures in which the component I and the component II are alternately and cross-like arranged in both the lateral and longitudinal directions.

8. The application according to claim 4, wherein the esterification reaction refers to esterification of propionic acid and n-propanol; and the transesterification reaction refers to transesterification reaction of isopropyl acetate and methanol.

* * * * *